United States Patent [19]
Ikejiri et al.

[11] Patent Number: 5,419,898
[45] Date of Patent: May 30, 1995

[54] ANTIALLERGIC COMPOSITION FOR OPHTHALMIC OR NASAL USE

[75] Inventors: Yoshifumi Ikejiri, Ibaraki; Takahiro Ogawa, Nishinomiya; Fuminori Tokumochi; Shogo Sameshima, both of Kobe; Motoko Kimura, Takarazuka, all of Japan

[73] Assignee: Senju Pharmacuetical Co., Ltd., Osaka, Japan

[21] Appl. No.: 169,706

[22] Filed: Dec. 20, 1993

[30] Foreign Application Priority Data

Dec. 25, 1992 [JP] Japan .................. 4-346031

[51] Int. Cl.$^6$ ............................. A61K 31/495
[52] U.S. Cl. ................. 424/78.04; 514/912; 514/914
[58] Field of Search ............ 514/912, 772.3, 914; 424/78.04

[56] References Cited

U.S. PATENT DOCUMENTS

| | | | |
|---|---|---|---|
| 4,525,358 | 6/1985 | Baltes et al. | 514/255 |
| 5,188,826 | 2/1993 | Chandrasekaran et al. | 514/912 |
| 5,192,780 | 3/1993 | York et al. | 514/912 |

FOREIGN PATENT DOCUMENTS

| | | |
|---|---|---|
| 0292050 | 11/1988 | European Pat. Off. . |
| 0433766 | 6/1991 | European Pat. Off. . |
| 0468392 | 1/1992 | European Pat. Off. . |

OTHER PUBLICATIONS

Medline Abstract 90:506678, Herman et al., Jul. 1990.
Medline Abstract 90:506680.
Medline Abstract 9333171 Stock et al., 1993.
Medline 88:216500, Broide et al., Mar. 1988.
Francillon et al., J. Allergy Clin. Immunol., vol. 91, No. I-2, Jan. 1993, p. 258.
Braunstein et al., Br. J. Clin. Pharmac., vol. 33, No. 4, 1992, pp. 445–448.

*Primary Examiner*—Thurman K. Page
*Assistant Examiner*—Peter F. Kulkosky
*Attorney, Agent, or Firm*—Wenderoth, Lind & Ponack

[57] ABSTRACT

There is disclosed an antiallergic composition for ophthalmic or nasal use, comprising cetirizine or a salt thereof as an active ingredient. The antiallergic composition may further contain a cyclodextrin compound, as well as a surfactant and/or a water soluble polymer.

16 Claims, No Drawings

ANTIALLERGIC COMPOSITION FOR OPHTHALMIC OR NASAL USE

FIELD OF THE INVENTION

The present invention relates to an antiallergic composition for ophthalmic or nasal use, and more particularly, it relates to a cetirizine-containing antiallergic composition which is useful for the treatment of allergic diseases in the fields of ophthalmology and otorhinology.

BACKGROUND OF THE INVENTION

Cetirizine is an antiallergic compound of the formula:

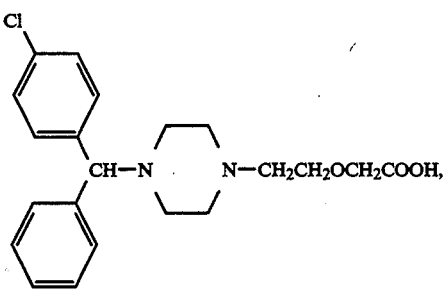

the chemical name of which is [2-[4-[(4-chlorophenyl)-phenylmethyl]-1-piperazinyl-]ethoxy]acetic acid.

Cetirizine is well known to have an antiallergic effect, for example, by oral administration, and it is particularly useful as an antiallergic agent with significant specificity to histamine (see, e.g., JP-B 63-11353).

In ophthalmic or nasal allergic diseases, taking the former as an example, systemic symptoms are frequently associated with ophthalmic symptoms, in which case the oral administration of an antiallergic agent is effective for their treatment. There are, however, some cases where no systemic abnormality can be detected even if marked changes are found in the eyes, and in particular, lesions found only in the eyes are not always accompanied by systemic abnormality. In such cases, topical therapy is preferred to systemic therapy because of its safety and effectiveness. This relationship between the systemic and topical symptoms holds true even in the field of otorhinology.

As an ophthalmic solution containing cetirizine, there is disclosed an antiallergic and antihistaminic composition (see, e.g., JP-A 4-9339). This composition comprises an antiallergic agent and an antihistaminic agent capable of exhibiting effective antihistaminic action when used in combination with the antiallergic agent. Cetirizine is exemplified as such an antihistaminic agent that is one of the essential ingredients of the composition.

However, no report has hitherto been made of an effect attained by the ophthalmic application of an antiallergic composition containing cetirizine as only one active ingredient.

Cetirizine has, although it is readily soluble in water, a disadvantage that a solution of cetirizine at low concentrations (below 1 w/v %) may cause the deposition of insoluble matter with the lapse of time, thereby decreasing the stability as an aqueous solution. This seems to be because cetirizine is one of the diphenylmethane derivatives capable of forming molecular aggregates (see, e.g., Masayuki Nakagaki (ed.), "Bussei-Butsuri (Material Science)," Nankodo, Tokyo, 1986, pp. 238-239). On the other hand, a solution of cetirizine at high concentrations where no insoluble matter will be deposited has strong irritating properties when applied in ophthalmic or nasal use, and it cannot be used as an ophthalmic or nasal solution. For this reason, there has not yet been developed an antiallergic composition for practical use containing cetirizine as the main active ingredient, which can be applied as an ophthalmic or nasal solution.

In general, it is difficult in most cases to prepare an ophthalmic or nasal solution with satisfactory safety and stability from a drug having irritating properties or capable of forming molecular aggregates, although it depends on the kind of the drug used.

Cyclodextrin compounds are well known to have a property of taking various drugs into their central portion to form clathrate compounds of these drugs because they are cyclic sugars. Therefore, cyclodextrin compounds have hitherto been used for the purpose of making a solution of various slightly-soluble drugs or improving the stability of drugs. However, when a cyclodextrin compound is blended with a certain drug, it becomes difficult in most cases to exhibit the efficacy of the drug, and this problem is particularly serious for external preparations.

SUMMARY OF THE INVENTION

Under these circumstances, the present inventors have intensively studied to develop a cetirizine-containing ophthalmic or nasal solution with satisfactory safety and stability, which can overcome the above-described disadvantages of cetirizine and which has no irritating properties to eyes and nasal mucosae. As the result, they have found that the addition of a cyclodextrin compound to an aqueous solution of cetirizine can reduce the deposition of insoluble matter even at low concentrations where molecular aggregates of cetirizine will be found in conventional cases. They have also found that an aqueous solution of cetirizine blended with a cyclodextrin compound can suppress the irritation of cetirizine to eyes or nasal mucosae even at high concentrations where such an irritation will be found in conventional cases, and that such an aqueous solution can maintain a sufficient inhibitory effect on allergic diseases of ocular or nasal portions. Further, they have found that the addition of a surfactant and/or a water-soluble polymer to an aqueous solution of cetirizine blended with a cyclodextrin compound can prevent the association of cetirizine in the aqueous solution for a long period of time. Thus, they have completed the present invention.

That is, the present invention provides an antiallergic composition for ophthalmic or nasal use, characterized in that it comprises cetirizine or a salt thereof as an active ingredient. It may further contain a cyclodextrin compound, as well as a surfactant and/or a water-soluble polymer.

The antiallergic composition of the present invention has almost no irritation to eyes and nasal mucosae, and it can be effectively used as a prophylactic and therapeutic agent for allergic diseases in the fields of ophthalmology and otorhinology, such as allergic conjunctivitis (e.g., conjunctival pollinosis), vernal conjunctivitis, uveitis and allergic rhinitis.

DETAILED DESCRIPTION OF THE INVENTION

The antiallergic composition of the present invention contains cetidzine or a salt thereof as an active ingredient. Examples of the salt of cetirizine are inorganic acid salts such as hydrochloride, sulfate, nitrate and phosphate; and organic acid salts such as acetate, citrate, tartrate and maleate.

The antiallergic composition of the present invention may further contain a cyclodextrin compound, as well as a surfactant and/or a water-soluble polymer.

Typical examples of the cyclodextrin compound are α-cyclodextrin, β-cyclodextrin, γ-cyclodextrin, hydroxypropyl β-cyclodextrin, dimethyl β-cyclodextrin, maltosyl β-cyclodextrin and β-cyclodextrin sulfate. Particularly preferred are α-cyclodextrin, β-cyclodextrin and γ-cyclodextrin. These cyclodextrin compounds may be used alone or in combination.

The amount of cyclodextrin compound to be used may vary with its solubility and the concentration of cetirizine. It is, however, desirable that the amount of cyclodextrin compound is 0.5 to 3.0 moles, preferably 1.0 to 2.0 moles, as much as the mole of cetirizine.

The surfactants are preferably of the non-ionic type. Typical examples of the non-ionic surfactant are polysorbate 80, polyoxyethylene hydrogenated castor oil 50 and polyoxyethylene hydrogenated castor oil 60. These surfactants may be used alone or in combination.

The water-soluble polymer includes cellulose derivatives, vinyl polymers and polyols. Examples of the cellulose derivative are alkylcelluloses such as methylcellulose and carboxymethylcellulose; and hydroxyalkylcelluloses such as hydroxypropylcellulose and hydroxyethylcellulose. Typical examples of the vinyl polymer are polyvinyl pyrrolidone and polyvinyl alcohol. Typical examples of the polyol are a series of macrogol 200 to 6000. These water-soluble polymers may be used alone or in combination.

The amount of surfactant or water-soluble polymer to be used may vary with its kind and the concentration of cetirizine. It is, however, desirable that the amount of surfactant is 0.01 to 1.0 time, preferably 0.05 to 0.5 times, as much as the weight of cetirizine, and the amount of water-soluble polymer is 0.01 to 10.0 times, preferably 0.02 to 5.0 times, as much as the weight of cetirizine.

The antiallergic composition of the present invention can be used within the pH range adopted for ordinary ophthalmic or nasal solutions, and it is usually adjusted to pH 4.0 to 9.0, preferably pH 5.0 to 8.0.

The antiallergic composition of the present invention may further contain any conventional additives in suitable amounts, which are used in ordinary ophthalmic or nasal solutions, e.g., preservatives such as p-hydroxybenzoates, benzalkonium chloride and chlorobutanol; chelating agents such as disodium edetate and sodium citrate; agents for making isotonic solutions, such as sodium chloride, sorbitol and glycerin; buffer agents such as phosphates, boric acid and citrates; and pH controlling agents such as hydrochloric acid, acetic acid and sodium hydroxide. The amount of additive to be used can be determined by those skilled in the art within the same range as adopted for ordinary ophthalmic or nasal solutions.

The antiallergic composition of the present invention may further contain any therapeutic ingredients other than cetirizine in suitable amounts, so long as the excellent advantages attained by the present invention are not deteriorated.

The antiallergic composition of the present invention may have various dosage forms which are pharmaceutically acceptable in the field of ophthalmology or otorhinology, such as solutions, suspensions, emulsions, gels and ointments. It may also be prepared, for example, in aqueous solution form and then lyophilized in powder form, which is reconstructed into an aqueous solution with distilled water at the time of use.

The concentration of cetirizine in the antiallergic composition of the present invention may vary with the administration route and allergic symptoms. It is, however, usually in the range of about 0.01 to 4.0 w/v%, preferably about 0.05 to 2.0 w/v %. For example, when used as an ophthalmic solution for adult patients, the antiallergic composition of the present invention is preferably administered about 3 to 6 times a day in a dose of one to several drops at each time. When used as a nasal solution, the antiallergic composition of the present invention is preferably atomized and inhaled about 3 to 6 times a day in a dose of 1 to 2 sprays at each time into the nasal cavity with an atomizer.

The present invention will be further illustrated by way of the following test examples and working examples, which are not to be construed to limit thereof.

Test Example 1: Eye irritation test in rabbits (Method)

Using male Japanese white rabbits without any abnormality in the anterior parts of their eyes (4 groups of 3 rabbits), Composition C, D, E or F prepared in solution form according to the formulation shown in Table 1 was instilled into the right eyes of the rabbits in the corresponding group and only the vehicle into their left eyes 8 times a day at 1-hour intervals in a dose of one drop at each time for 5 days. For evaluation, a macroscopic examination of the anterior parts of the eyes and a corneal fluorescein staining assay were performed before the first instillation on day 1, 30 minutes after the last instillation on each of days 1, 3 and 5 of treatment, and on day 6.

TABLE 1

| Ingredient (w/v %) | Compositions | | | | | | | | | |
|---|---|---|---|---|---|---|---|---|---|---|
| | A | B | C | D | E | F | G | H | J | K |
| Active ingredient Cetirizine hydrochloride | 0.25 | 0.4 | 0.5 | 1.0 | 1.0 | 1.0 | 1.0 | 1.0 | 1.0 | 2.0 |
| Additional ingredients | | | | | | | | | | |
| α-Cyclodextrin | — | — | — | — | 2.1 | — | — | — | — | — |
| β-Cyclodextrin | — | — | — | — | — | 2.45 | — | — | — | 4.9 |
| γ-Cyclodextrin | — | — | — | — | — | — | 2.81 | — | — | — |
| Polyvinyl pyrrolidone | — | — | — | — | — | — | — | 2.05 | — | — |
| Chlorobutanol | — | — | — | — | — | — | — | — | 0.3 | — |
| Vehicle | | | | | | | | | | |
| Conc. glycerin | 2.0 | 2.0 | 2.0 | 2.0 | 2.0 | 2.0 | 2.0 | 2.0 | 2.0 | 2.0 |

TABLE 1-continued

| Ingredient | Compositions | | | | | | | | | |
|---|---|---|---|---|---|---|---|---|---|---|
| (w/v %) | A | B | C | D | E | F | G | H | J | K |
| Boric acid | 0.4 | 0.4 | 0.4 | 0.4 | 0.4 | 0.4 | 0.4 | 0.4 | 0.4 | 0.4 |
| Sodium hydroxide | q.s. | q.s. | q.s. | q.s. | q.s. | q.s. | q.s. | q.s. | q.s. | q.s. |
| pH | 7.0 | 7.0 | 7.0 | 7.0 | 7.0 | 7.0 | 7.0 | 7.0 | 7.0 | 7.0 |

(Results)

In the groups of rabbits topically dosed with Solution C or D, redness was observed on the palpebral conjunctiva and nictitating membrane after the last instillation on day 1. Particularly, in the group of rabbits given Solution D, their symptoms were so severe that individual blood vessels to be clearly observed on the normal palpebral conjunctiva were not definitely discernible. In addition, bulbar conjunctival vasodilation and palpebral conjunctival edema were observed. The redness as mentioned above was still observed even 16 hours after the last administration on day 1 and up to the beginning of instillation on day 2. The observation on day 3 of treatment also found redness of the conjunctiva as in the observation after the last instillation on day 1 but with an increased severity in both groups, indicating that cetirizine has a strong irritating effect on the conjunctiva. In the corneal fluorescein stain assay performed at the completion of instillation treatment, dye spots were observed over the entire corneal area in both groups, indicating that cetirizine also irritates the corneal epithelium. Judging that the rabbit eyes could not tolerate further instillation, the treatment with Solution C or D was discontinued on day 3.

In the group of rabbits given Solution E containing a cyclodextrin compound, slight redness was observed on the palpebral and bulbar conjunctivae after the last instillation on day 1, while very small amounts of discharge were found in some rabbits of the group dosed with Solution F. However, neither the redness nor the eye discharge as found on day 1 was observed on and after day 3. Even in the corneal fluorescein staining assay done at the end of treatment, no change was found from the condition before the treatment and all the findings were invariably within the normal range, clearly indicating that a reduction in ocular irritation can be attained by the addition of a cyclodextrin compound to a composition of cetirizine hydrochloride. The eyes treated with the vehicle showed no sign of irritation caused by the vehicle.

Test Example 2: Toxicity test by instillation into rabbit eyes (Method)

Using male Japanese white rabbits in good health without any abnormality in the ophthalmological examination (2 groups of 5 rabbits), ophthalmic composition F or K prepared in solution form according to the formulation shown in Table 1 was instilled into both eyes of the rabbits in the corresponding group 8 times a day in a dose of one drop at each time for 28 days. The rabbits were examined for the general condition, food consumption, body weight and ophthalmological items (macroscopic observation of the anterior part of eyes, observation of the corneal stained spots and fundus oculi, measurement of the intraocular tension) with the lapse of time for 28 days, after which they were subjected to urinalysis, hematological examination, blood chemical examination, autopsy, organ weight measurement, histopathological examination of the eyeball and electron microscopic examination of the cornea.

(Results)

With respect to the installation of Solution F or K, no abnormality was found in the ophthalmological examination, general condition and other examinations.

Test Example 3: Effect on rat histamine-induced conjunctivitis (Method)

Male Wistar rats of about 100 g in weight were injected subconjunctivally each with 50 $\mu$l of 0.1 w/v % histamine at the upper eyelid. Each of the following test ophthalmic compositions in solution form was instilled into both eyes of the rats in the corresponding group at a dose of 3 $\mu$l for each eye 40 and 20 minutes before the histamine injection. The rats were sacrificed one hour after the histamine injection. The palpebral conjunctival edema weight was measured, and the edema inhibition rate was calculated using the edema weight of the physiological saline group as the maximal response. As the test ophthalmic solutions, a solution prepared by dissolving cetirizine hydrochloride in the vehicle (2.0 w/v % conc. glycerin, 0.4 w/v % aqueous boric acid and sodium hydroxide (q.s.); pH 7.0) to have a specified final concentration (hereinafter referred to as CE ophthalmic solution), a solution prepared by dissolving equimolar amounts of cetirizine hydrochloride and either $\alpha$- or $\beta$-cyclodextrin in the vehicle at a specified final concentration (hereinafter referred to as CE+$\alpha$-CD ophthalmic solution and CE+$\beta$-CD ophthalmic solution, respectively) and a solution prepared by dissolving diphenhydramine hydrochloride in the vehicle (hereinafter referred to as DPH ophthalmic solution) were used.

(Results)

In the rat model of histamine-induced conjunctivitis, cetirizine hydrochloride exhibited an inhibition rate of about 88.8% at the concentration of 0.5 w/v %, indicating that cetirizine hydrochloride has a sufficient antihistaminic effect even when topically used in the field of ophthalmology.

To compare the efficacy against histamine-induced conjunctivitis of cetirizine hydrochloride when formulated with $\alpha$- or $\beta$-cyclodextrin, the cetirizine hydrochloride concentration (mM) of each ophthalmic solution which exhibited a 50% inhibition of the edema (IC$_{50}$) was determined using the edema rate of the physiological saline-instilled rat group as a control. The IC$_{50}$ values obtained for the test ophthalmic solutions are shown in Table 2.

TABLE 2

Inhibitory-Effect of Cetirizine on Histamine-induced Conjunctivitis

| Test ophthalmic solution | IC$_{50}$* |
|---|---|
| CE | 2.05 mM |
| CE + $\alpha$-CD | 1.97 |
| CE + $\beta$-CD | 2.76 |

TABLE 2-continued

Inhibitory-Effect of Cetirizine on
Histamine-induced Conjunctivitis

| Test ophthalmic solution | IC$_{50}$* |
|---|---|
| DPH | 120.0 |

*The concentration of cetirizine hydrochloride which gives 50% inhibition of histamine-induced rat conjunctivitis.

As shown in Table 2, the IC$_{50}$ value of CE ophthalmic solution was 2.05 mM (about 0.1 w/v %), indicating that cetirizine hydrochloride has an antihistaminic effect to a certain extent even below irritating concentrations. The groups of rats treated with CE or CE+α-CD ophthalmic solution gave substantially equal IC$_{50}$ values, indicating that, in this experimental system, α-cyclodextrin does not substantially affect the efficacy of cetirizine hydrochloride. The IC$_{50}$ value in the group of rats treated with CE+β-CD ophthalmic solution was somewhat higher than that found in the group of rats treated with CE ophthalmic solution (containing cetirizine hydrochloride alone). This fact suggests that the addition of β-cyclodextrin to a composition of cetirizine hydrochloride causes a slight decrease in the efficacy of cetirizine hydrochloride in this experimental system but the degree of decrease is so small that the efficacy of cetirizine hydrochloride can be well maintained.

Test Example 4: Eye irritation test in humans (Method)

There is some difference in irritation response between the human and animal eyes when an ophthalmic solution is instilled thereinto. In addition, some subjective factors such as a feeling after the use should be considered in case of human eyes. It is, therefore, be concluded that ophthalmic solutions without any irritation to human eyes are more preferred, and any strongly irritative composition cannot be put to practical use. In this regard, Compositions A, B, D, E, F, G, H, J and K in solution form as shown in Table 1 were evaluated for the feeling after their use when instilled into the eyes of human subjects (I, II, III and IV). The results are shown in Table 3.

TABLE 3

| Ophthalmic composition | Irritation to Human Eyes | | | |
|---|---|---|---|---|
| | Human subjects | | | |
| | I | II | III | IV |
| A | − | + | − | + |
| B | + | + | ++ | ++ |
| D | +++ | +++ | +++ | +++ |
| E | − | − | − | − |
| F | − | − | − | − |
| G | − | − | − | − |
| H | +++ | ++ | +++ | +++ |
| J | +++ | +++ | +++ | +++ |
| K | − | − | − | − |

−: No irritation or discomfort
+: Slight irritation
++: Moderate irritation (pain)
+++: Strong irritation (Results)

Among the cyclodextrin-free ophthalmic compositions, i.e., Compositions A, B and D in solution form, Solution A containing 0.25 w/v % cetirizine hydrochloride gave slight irritation only to two of four subjects, indicating that the irritation of cetirizine hydrochloride to human eyes is significantly reduced at relatively low concentrations. In contrast, Solutions B and D both having a cetirizine hydrochloride concentration of 0.4 w/v % or more gave irritation to all the subjects, and in particular, Solution D was so much irritative that it has no practical use.

On the other hand, Solutions E, F, G and K each containing α-, β- or γ-cyclodextrin caused no ocular irritation, although their cetirizine hydrochloride concentrations were as high as 1 w/v %. It was, therefore, clear that the addition of a cyclodextrin compound to a composition of cetirizine hydrochloride can reduce the irritation response of eyes to cetirizine hydrochloride and the resulting composition in solution form can be used safely as an ophthalmic solution.

Solution H containing polyvinyl pyrrolidone which caused no ocular irritation but has the property of forming complexes with many different substances, and Solution J containing chlorobutanol which has local anesthetic action and is usually used for reducing the local pain caused by an injection, gave strong ocular irritation, indicating that neither polyvinyl pyrrolidone nor chlorobutanol is suitable as an additional ingredient for the object of the present invention, that is, for suppressing ocular irritation caused by cetirizine or salts thereof.

Test Example 5: Human Nasal Mucosal Irritation Test (Method)

It can also be said that nasal solutions without any irritation to human noses are more preferred as is true of ophthalmic solutions, and any strongly irritative composition cannot be put to practical use. In this regard, Solutions C, D and F were evaluated for the feeling after their use when sprayed into the noses of human subjects (I, II and III). The results are shown in Table 4.

TABLE 4

| Ophthalmic composition | Irritation to Human Noses | | |
|---|---|---|---|
| | Human subjects | | |
| | I | II | III |
| C | − | + | − |
| D | ++ | +++ | +++ |
| F | − | − | + |

−: No irritation or discomfort
+: Slight irritation
++: Moderate irritation (pain)
+++: Strong irritation (Results)

When Solution C was sprayed into the nose, one of three subjects felt it irritative. When Solution D was applied, all the subjects felt strong irritation which persisted for a fairly long time, indicating that a composition containing only cetirizine hydrochloride in the vehicle is also irritative to nasal mucosae.

On the other hand, Solution F containing β-cyclodextrin gave slight irritation only to one of three subjects, although the cetiridine hydrochloride concentration thereof was the same as that of Solution D giving strong irritation. Moreover, the irritation from Solution F disappeared in a brief time. It is, therefore, clear that the addition of a cyclodextrin compound to a composition of cetirizine or a salt thereof can suppress the irritation to nasal mucosae and such a composition in solution form can be used as a nasal solution.

Test Example 6: Stability Test (Method)

Compositions A and K shown in Table 1; and Compositions L to N and P to R shown in Table 5 were prepared in solution form. Each of the solutions was filtered through a membrane filter of 0.45 μm mesh, followed by filling into a glass ampoule. These ampoules were stored at room temperature for 6 months, during which they were subjected to macroscopic observation for the presence of insoluble matter with the lapse of time.

TABLE 5

| Ingredient (w/v %) | Compositions | | | | | |
|---|---|---|---|---|---|---|
| | L | M | N | P | Q | R |
| Active ingredient | 0.25 | 2.0 | 2.0 | 2.0 | 2.0 | 2.0 |
| Cetirizine hydrochloride | | | | | | |
| Additional ingredients | | | | | | |
| β-Cyclodextrin | 0.61 | 4.9 | 4.9 | 4.9 | 4.9 | 4.9 |
| Hydroxypropylmethyl-cellulose | — | 0.2 | — | — | — | — |
| Polyvinyl alcohol | — | — | 0.2 | — | — | — |
| Polysorbate 80 | — | — | — | 0.2 | — | — |
| Polyvinyl pyrrolidone | — | — | — | — | 2.0 | — |
| Macrogol 4000 | — | — | — | — | — | 1.0 |
| Vehicle | | | | | | |
| Conc. glycerin | 2.0 | 2.0 | 2.0 | 2.0 | 2.0 | 2.0 |
| Boric acid | 0.4 | 0.4 | 0.4 | 0.4 | 0.4 | 0.4 |
| Sodium hydroxide | q.s. | q.s. | q.s. | q.s. | q.s. | q.s. |
| pH | 7.0 | 7.0 | 7.0 | 7.0 | 7.0 | 7.0 |

(Results)

The deposition of insoluble matter was observed in the ampoule of Solution A after one day from the beginning of the storage at room temperature. The ampoules of Solution K and L exhibited a slight deposition of insoluble matter after six months. In contrast, no deposition of insoluble matter was found in the ampoules of Solution M, N and P to R even after six months.

It was, therefore, found that the addition of a cyclodextrin compound to a composition of cetirizine hydrochloride can reduce the association of cetirizine and the addition of a surfactant or a water-soluble polymer to a composition of cetirizine hydrochloride and a cyclodextrin compound can prevent the association of cetirizine, thereby making it possible to obtain an antiallergic composition in stable solution form. It was also found that a combination of cetirizine hydrochloride only with a surfactant or a water-soluble polymer cannot prevent the deposition of insoluble matter.

EXAMPLE 1

An ophthalmic composition was prepared in lyophilized powder form according to the following formulation:

| Ingredient | Amount |
|---|---|
| Cetirizine hydrochloride | 0.5 g |
| Boric acid | 5.0 g |
| Sodium hydroxide | q.s. |
| Distilled water | ad 100 ml |

Cetirizine hydrochloride and boric acid are dissolved in about 80 ml of distilled water, and the solution is adjusted to pH 7.0 by the addition of aqueous sodium hydroxide, to which distilled water is further added to have a total volume of 100 ml. The solution thus obtained is sterilized by filtration, and dispensed in 2 ml portions, which are then lyophilized, resulting in an ophthalmic composition. At the time of use, the ophthamic composition is dissolved in 5 ml of distilled water for injection.

EXAMPLE 2

An ophthalmic composition was prepared in solution form according to the following formulation:

| Ingredient | Amount |
|---|---|
| Cetirizine hydrochloride | 1.0 g |
| α-cyclodextrin | 2.1 g |
| Boric acid | 2.0 g |
| Sodium hydroxide | q.s. |
| Distilled water | ad 100 ml |

Cetirizine hydrochloride, α-cyclodextrin and boric acid are dissolved in about 80 ml of distilled water, and the solution is adjusted to pH 7.0 by the addition of aqueous sodium hydroxide, to which distilled water is further added to have a total volume of 100 ml, resulting in an ophthalmic composition.

EXAMPLE 3

An ophthalmic composition was prepared in solution form according to the following formulation:

| Ingredient | Amount |
|---|---|
| Cetirizine hydrochloride | 1.0 g |
| α-cyclodextrin | 2.1 g |
| Hydroxypropylmethylcellulose | 0.1 g |
| Boric acid | 2.0 g |
| Sodium hydroxide | q.s. |
| Distilled water | ad 100 ml |

About 80 ml of distilled water is heated to about 90° C., in which hydroxypropylmethylcellulose is uniformly dispersed. The dispersion is stirred in an ice-water bath so that the hydroxypropylmethylcellulose is dissolved. After warming to room temperature, cetirizine hydrochloride, α-cyclodextrin and boric acid are dissolved in the solution. The solution thus obtained is adjusted to pH 7.0 by the addition of aqueous sodium hydroxide, to which distilled water is further added to have a total volume of 100 ml, resulting in an ophthalmic composition.

EXAMPLE 4

A nasal composition was prepared in solution form according to the following formulation:

| Ingredient | Amount |
|---|---|
| Cetirizine hydrochloride | 2.0 g |
| β-cyclodextrin | 4.93 g |
| Hydroxypropylmethylcellulose | 0.2 g |
| Boric acid | 2.5 g |
| Disodium edetate | 0.02 g |
| Sodium hydroxide | q.s. |
| Distilled water | ad 100 ml |

About 80 ml of distilled water is heated to about 90° C., in which hydroxypropylmethylcellulose is uniformly dispersed. The dispersion is stirred in an ice-water bath so that the hydroxypropylmethylcellulose is dissolved. After warming to room temperature, cetirizine hydrochloride, β-cyclodextrin, boric acid and disodium edetate are dissolved in the solution. The solution thus obtained is adjusted to pH 7.0 by the addition of aqueous sodium hydroxide, to which distilled water is further added to have a total volume of 100 ml, resulting in a nasal composition.

EXAMPLE 5

An ophthalmic composition was prepared in solution form according to the following formulation:

| Ingredient | Amount |
| --- | --- |
| Cetirizine hydrochloride | 0.3 g |
| α-cyclodextrin | 0.8 g |
| Polyvinyl alcohol | 0.2 g |
| Sodium acetate | 0.1 g |
| Propylene glycol | 2.0 g |
| Methylparaben | 0.2 g |
| Propylparaben | 0.1 g |
| Sodium hydroxide | q.s. |
| Distilled water | ad 100 ml |

About 80 ml of distilled water is heated to about 90° C., in which polyvinyl alcohol, methylparaben and propylparaben are dissolved. After cooling to room temperature, cetirizine hydrochloride, a-cyclodextrin, sodium acetate and propylene glycol are dissolved in the solution. The solution thus obtained is adjusted to pH 7.0 by the addition of aqueous sodium hydroxide, to which distilled water is further added to have a total volume of 100 ml, resulting in an ophthalmic composition.

EXAMPLE 6

A nasal composition was prepared in solution form according to the following formulation:

| Ingredient | Amount |
| --- | --- |
| Cetirizine hydrochloride | 1.0 g |
| β-cyclodextrin | 2.47 g |
| Hydroxypropylmethylcellulose | 0.1 g |
| Boric acid | 1.25 g |
| Disodium edetate | 0.01 g |
| Sodium hydroxide | q.s. |
| Distilled water | ad 100 ml |

About 80 ml of distilled water is heated to about 90° C., in which hydroxypropylmethylcellulose is uniformly dispersed. The dispersion is stirred in an ice-water bath so that the hydroxypropylmethylcellulose is dissolved. After warming to room temperature, cetirizine hydrochloride, β-cyclodextrin, boric acid and disodium edetate are dissolved in the solution. The solution thus obtained is adjusted to pH 7.0 by the addition of aqueous sodium hydroxide, to which distilled water is further added to have a total volume of 100 ml, resulting in a nasal composition.

EXAMPLE 7

A nasal composition was prepared in solution form according to the following formulation:

| Ingredient | Amount |
| --- | --- |
| Cetirizine hydrochloride | 0.5 g |
| Hydroxypropyl β-cyclodextrin | 1.6 g |
| Polyvinyl pyrrolidone | 1.0 g |
| Macrogol 4000 | 1.0 g |
| Potassium dihydrogenphosphate | 0.1 g |
| Mannitol | 5.1 g |
| Benzalkonium chloride | 0.005 g |
| Potassium hydroxide | q.s. |
| Distilled water | ad 100 ml |

Cetirizine hydrochloride, hydroxypropy β-cyclodextrin, polyvinyl pyrrolidone, macrogol 4000, potassium dihydrogenphosphate, mannitol and benzalkonium chloride are dissolved in about 80 ml of distilled water. The solution thus obtained is adjusted to pH 7.5 by the addition of aqueous potassium hydroxide, to which distilled water is further added to have a total volume of 100 ml, resulting in a nasal composition.

EXAMPLE 8

A nasal composition was prepared in solution form according to the following formulation:

| Ingredient | Amount |
| --- | --- |
| Cetirizine hydrochloride | 1.0 g |
| α-cyclodextrin | 1.0 g |
| β-cyclodextrin | 1.5 g |
| Sodium citrate | 0.05 g |
| Sodium chloride | 0.9 g |
| Potassium hydroxide | q.s. |
| Distilled water | ad 100 ml |

Cetirizine hydrochloride, α-cyclodextrin, β-cyclodextrin, sodium citrate and sodium chloride are dissolved in about 80 ml of distilled water. The solution thus obtained is adjusted to pH 6.5 by the addition of aqueous potassium hydroxide, to which distilled water is further added to have a total volume of 100 ml, resulting in a nasal composition.

What is claimed is:

1. An antiallergic ophthalmic or nasal composition, comprising an effective amount of a compound of the formula

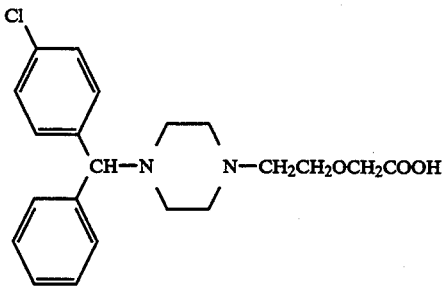

or a pharmaceutically acceptable salt thereof as an active ingredient, and a cyclodextrin compound in an amount of about 1.0 to 2.0 moles per mole of the compound of the above formula or salt thereof.

2. An antiallergic composition according to claim 1 wherein said cyclodextrin compound is selected from the group consisting of α-cyclodextrin, β-cyclodextrin and γ-cyclodextrin.

3. An antiallergic composition according to claim 1, further comprising a surfactant in an amount of about 0.05 to 0.5 times the weight of the compound of the formula or salt thereof.

4. An antiallergic composition according to claim 1, further comprising a water-soluble polymer in an amount of about 0.02 to 5.0 times the weight of the compound of the formula or salt thereof.

5. An antiallergic composition according to claim 3, wherein said surfactant is non-ionic.

6. An antiallergic composition according to claim 5, wherein said non-ionic surfactant is selected from the group consisting of polysorbate 80 and polyoxyethylene hydrogenated castor oil.

7. An antiallergic composition according to claim 4, wherein said water soluble polymer is selected from the group consisting of alkyl cellulose, hydroxyalkyl, vinyl polymers and polyols.

8. An antiallergic composition according to claim 7, wherein said cellulose derivative is selected from the group consisting of alkylcelluloses and hydroxyalkylcelluloses.

9. An antiallergic composition according to claim 8, wherein said alkylcellulose is selected from the group consisting of methylcellulose and carboxymethylcellulose.

10. An antiallergic composition according to claim 8, wherein said hydroxyalkylcellulose is selected from the group consisting of hydroxypropylmethylcellulose and hydroxyethylcellulose.

11. An antiallergic composition according to claim 7, wherein said vinyl polymer is selected from the group consisting of polyvinyl alcohol and polyvinyl pyrrolidone.

12. An antiallergic composition according to claim 7, wherein said polyol is macrogol 4000.

13. An antiallergic composition according to claim 3, further comprising a water-soluble polymer in an amount of about 0.02 to 5.0 times the weight of the compound of the formula or a salt thereof.

14. A method for the treatment of an ophthalmic or nasal allergic disease which comprises topically administering to the eye or to the nasal cavity of a patient in need of such treatment an effective amount of a composition according to claim 15.

15. A method according to claim 14, wherein the composition further contains a surfactant in an amount of about 0.05 to 0.5 times the weight of the compound of the formula or salt thereof.

16. A method according to claim 14, wherein the composition further contains a water-soluble polymer in an amount of about 0.02 to 5.0 times the weight of the compound of the formula or salt thereof.

* * * * *